United States Patent [19]
Schrenk et al.

[11] Patent Number: 5,713,128
[45] Date of Patent: Feb. 3, 1998

[54] ELECTROSURGICAL PAD APPARATUS AND METHOD OF MANUFACTURE

[75] Inventors: Charles Thomas Schrenk, Lafayette; Douglas Phil Talmage, Boulder, both of Colo.

[73] Assignee: Valleylab Inc., Boulder, Colo.

[21] Appl. No.: 602,402

[22] Filed: Feb. 16, 1996

[51] Int. Cl.$^6$ ................... H01R 43/16; B23P 23/00
[52] U.S. Cl. ............... 29/885; 29/564.1; 29/564.6; 128/641; 156/226; 156/252; 156/291; 156/293
[58] Field of Search ............... 29/885, 877, 878, 29/825; 128/640, 641; 156/226, 252, 291, 293

[56] References Cited

U.S. PATENT DOCUMENTS

| | | | |
|---|---|---|---|
| 4,063,352 | 12/1977 | Bevilacqua | 29/877 X |
| 4,317,278 | 3/1982 | Carmon et al. | 29/878 |
| 4,393,584 | 7/1983 | Bare et al. | 29/877 |
| 4,409,981 | 10/1983 | Lundberg | 29/825 X |
| 4,524,775 | 6/1985 | Rasmussen | 29/878 X |
| 4,580,339 | 4/1986 | Ioffe | 29/825 |
| 4,699,146 | 10/1987 | Sieverding | |
| 4,750,482 | 6/1988 | Sieverding | |
| 4,795,516 | 1/1989 | Strand | 29/877 X |
| 5,226,225 | 7/1993 | Bryan et al. | 29/825 |

*Primary Examiner*—Carl J. Arbes
*Attorney, Agent, or Firm*—Peter C. Richardson; Lawrence C. Akers; Aaron Passman

[57] ABSTRACT

A method of making a return pad for an electrosurgical system comprises the following steps. A first step includes die cutting an electrically conductive foil on a backing using a rotary press to create a foil blank. A second step includes peeling the conductive foil from around the blank, and leaving the blank on its backing. A third step includes layering electrically conductive gel together with the die cut foil to form a layered sheet. A fourth step includes blanking the return pad from the layered sheet using a rotary die. The rotary die has cutting edges and a die packing material adjacent to at least a portion of the edges. The die packing material compresses the gel prior to cutting. The compression is preferably sufficient to cause elastic deformation in the gel so that the gel retracts after being cut. The retraction of the gel leaves a border around the edge of the pad. The border region helps prevent the possibility of the gel coming into electrical contact with an unintended object. One of the advantages of the method of manufacturing disclosed herein is that a continuous rotary process can be used to manufacture electrosurgical return pads. The continuous nature of the process increases the efficiency of the manufacturing operation. The apparatus for using the method is also disclosed.

15 Claims, 3 Drawing Sheets

ELECTROSURGICAL PAD APPARATUS AND METHOD OF MANUFACTURE

FIELD OF THE INVENTION

This relates to a method of manufacturing an electrical return pad for an electrosurgical system, and more particularly to an improved method of manufacturing a return pad in a continuous rotary process.

BACKGROUND OF THE INVENTION

Electrosurgical systems are used by surgeons to cut and coagulate tissue of a patient. High frequency electrical current is conducted from a generator, through the tissue of the patient, and returns to the generator through an isolated return pad. This pad is typically located on the patient's skin at a site remote from the surgery. The return pad is electrically connected to the generator to complete a circuit through the patient.

Several kinds of return pads are presently available. For example, Valleylab, Inc. in Boulder, Colo. sells model number E7507 Disposable Patient Return Electrode. U.S. Pat. No. 4,699,146, assigned to Valleylab, covers a hydrophilic, elastomeric, pressure-sensitive adhesive which is used in the E7507 product. U.S. Pat. No. 4,750,482, also assigned to Valleylab, covers a wound dressing or burn dressing with a layer including the crosslinked water insoluble elastomeric pressure-sensitive gel which is similar to the gel used in the return pad. Generically, the material is an electrically conductive hydrogel sold under the trademark Polyhesive® manufactured by Valleylab of Boulder, Colo., the assignee of the present invention. These patents are hereby incorporated by reference and made a part of this disclosure.

Current manufacturing processes for return pads require a step-and-repeat method to apply discreet components, where each pad must stop momentarily along the manufacturing process. A step-and-repeat method slows the throughput of the manufacturing process and excludes many advantages which are available from a continuous rotary process.

Another practice in return pad manufacturing is to bond a border to the outer perimeter of the pad. One of the functions of the border is to insure that the electrically conductive gel does not spread to the edge of the pad where it could make an electrical connection with another object such as a bed frame. An electrical connection from the pad to some other conductive object could result in an electrical burn to the patient or surgical staff.

SUMMARY OF THE INVENTION

One of the advantages of the method of manufacturing disclosed herein is that a continuous rotary process can be used to manufacture electrosurgical return pads. The continuous nature of the process increases the efficiency of the manufacturing operation. Another advantage of the process is that less handling of the raw materials is required. Yet another advantage of the process is that a border piece is not required and thus fewer materials are used and less scrap is generated.

One of the important results from the manufacturing process is that the conductive gel layer is handled in a way that causes it to retract from the edges of the die cut return pad. This prevents unintentional electrical contact with objects near the pad. It also eliminates the need for a protective border piece. Normally, in die cutting operations, there are plates around the punch which are called "stripper" or "stinger" plates. These are commonly used to hold the piece to the tooling. This "gates" the process to prevent the material from flowing away from the punch as the punch enters the piece. The process described herein differs from normal die cutting operations because the gating function is replaced by a compression function which deforms and extrudes the gel prior to die penetration. The compression is designed to cause elastic deformation, and preferably avoids any plastic deformation of the gel. The compression is achieved by using an appropriate die packing material with a thickness that exceeds the height of the cutting die.

The list of advantages cited herein is not exhaustive, and skilled artisans will appreciate that other competitive advantages may be realized from this disclosure.

A method of making a return pad for an electrosurgical system comprises the following steps. A first step includes die cutting an electrically conductive foil on a backing using a rotary press to create a foil blank. The foil blank may be two separate sections of foil. A second step includes peeling the conductive foil from around the blank, and leaving the blank on its backing. The peeled-away foil is sometimes called a matrix, and is a scrap byproduct of the manufacturing process. A third step includes layering electrically conductive gel together with the die cut foil to form a layered sheet. The layering is preferably accomplished by passing the layers through a rolling press to adhere the layers together.

A fourth step includes blanking the return pad from the layered sheet using a rotary die. The rotary die has cutting edges and a die packing material adjacent to at least a portion of the edges. There may be a tab extending from the pad, in which case it may not be necessary to use die packing material in the vicinity of the tab. The die packing material compresses the gel prior to cutting. The compression is preferably sufficient to cause elastic deformation in the gel so that the gel retracts after being cut. The retraction of the gel leaves a border around the edge of the pad. The border region helps prevent the possibility of the gel coming into electrical contact with an unintended object.

The cutting edges which blank out the pads have two sides: a side that corresponds with the blank, and a side that corresponds with the scrap matrix. The method of making the pad may also include the step of installing the die packing material adjacent to the cutting edges on the side that corresponds with the pad blank. There may also be a leading edge and a trailing edge on the die. The method of making the pad may include using packing material which is wider on the leading edge of the die than on the trailing edge of the die.

One potential problem associated with blanking the pads is that the layered sheet may adhere to the die. Thus, the method may comprise the additional step of forcing compressed air around at least one edge of the cutting die to prevent the layered sheet from sticking to the die. The compressed air may be forced through holes in the die cutting roller, and there may have to be holes through the die packing material to allow the compressed air to contact the blank.

The method of making the pads may also comprise the step of packing two different materials against the cutting die. The two materials may be layered on top of each other. Each material may be a polyurethane, but each layer may have a different durometer. The top layer may be a softer durometer than the bottom layer. Each layer of packing material may be a closed cell form of polyurethane. The total thickness of the packing material should be sufficient to cause retraction of the conductive gel without causing plastic deformation or leaving any of the conductive foil exposed.

An apparatus for making a return pad for an electrosurgical system may comprise the following elements: a first die cutting roller, a take-up, a rotary press, and a second die cutting roller with die packing material around the cutting die. The first die cutting roller is used for die cutting an electrically conductive foil on a backing. The take-up follows the die cutting process for peeling the scrap foil matrix from its backing. The rotary press layers the electrically conductive gel together with the die cut foil to form a layered sheet. The second die cutting roller blanks out the pads from the layered sheet. The apparatus includes a die packing material around at least a portion of the cutting edges on the second die cutting roller. The die packing material is sufficient to compress the gel prior to cutting and cause the gel to retract after being cut.

DETAILED DESCRIPTION OF THE INVENTION

Figure 2B:
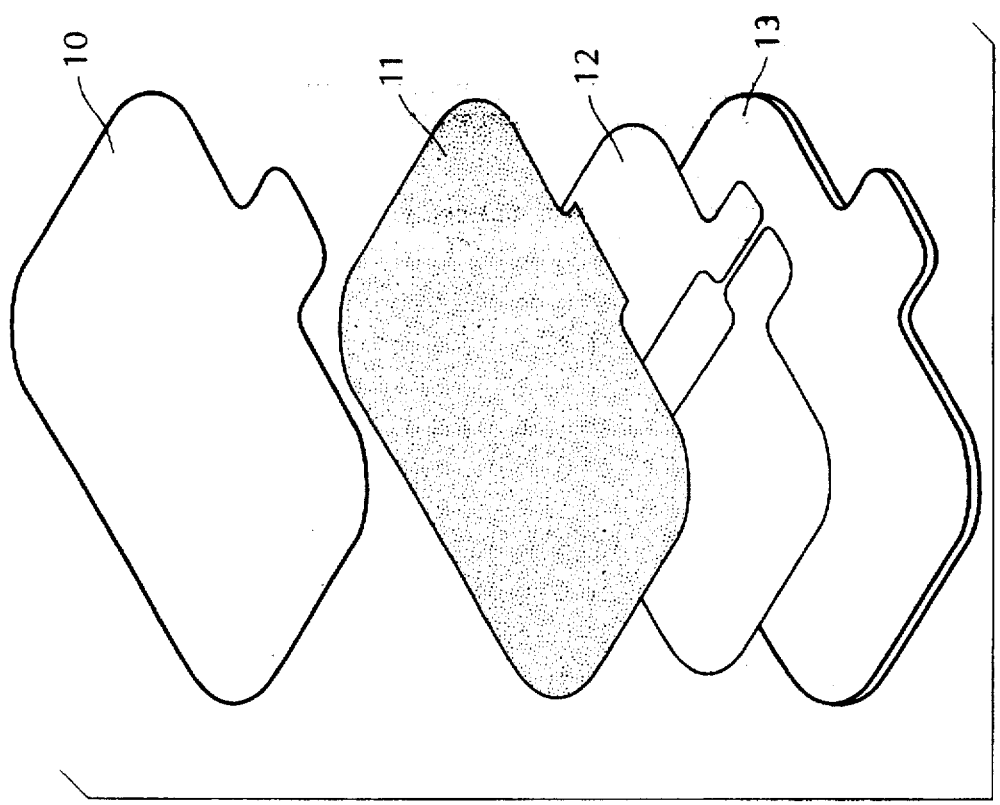
FIG. 2 is an exploded view of an electrosurgical pad which shows the layers of the laminate.
Figure 2A:
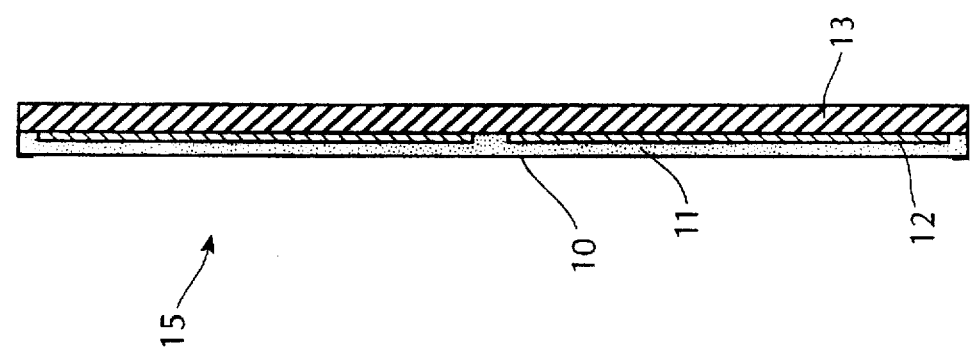

The patient return electrode 15 is a laminate composed of four layers, as shown in FIG. 2. The layers are as follows: the top layer is a removable release liner 10, followed by a layer of conductive gel adhesive 11, a conductive foil 12, and a non-conductive pad backing 13. The conductive foil 12 is preferably aluminum and is composed of two sections which are mounted adjacent to each other on the pad backing 13.

Figure 1:
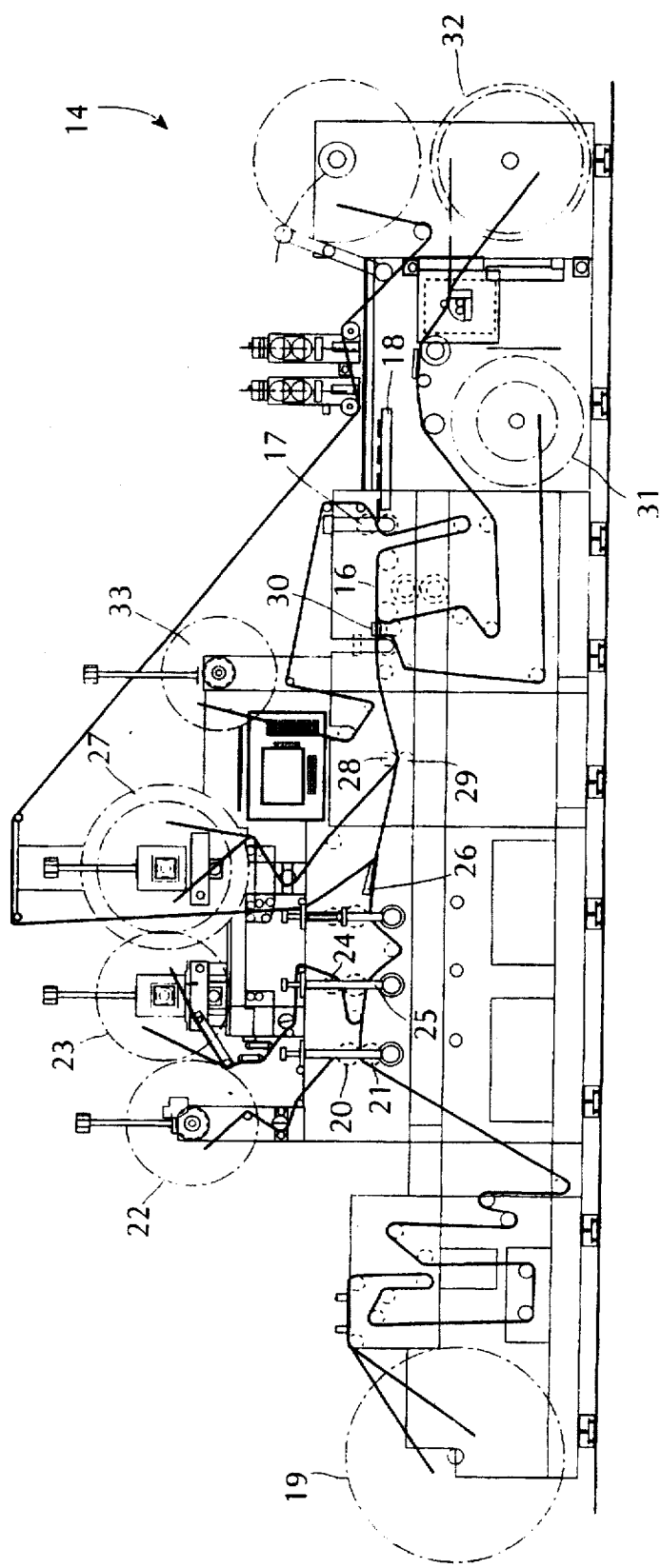
FIG. 1 is a schematic representation of a rotary conversion press which has been designed for electrosurgical pad manufacturing.

The preferred embodiment of the manufacturing apparatus and method uses a custom modified rotary conversion press 14, as shown in FIG. 1. The rotary conversion press 14 uses continuous motion to process various materials through sequential tooling stations. Raw materials are unwound from rollstock, die cut and laminated together to create a layered sheet 16 containing the various subassemblies needed to produce a return pad 15. Once the layered sheet 16 is created, the subassembly pad is die cut, or blanked, using a rotary press 17 and dispensed onto a conveyor 18 for further processing. The waste materials are wound up on rewinders and scraped.

The preferred machinery is a Mark Andy model 4120-10", manufactured by Mark Andy, Inc. of Chesterfield, Mo. The rotary converting press 14 has several stations where juxtaposed rollers, fitted with a die, are used to cut patterns in a continuous sheet. Other rollers in the press are used as tensioners, take-up and supply reels, and laminating stations.

The preferred embodiment of the method of making a return pad is partly illustrated in FIG. 1. Conductive foil stock, which is bonded to a carrier, is unwound from a foil supply reel 19. The foil is die cut as it passes through die cutting rollers 20 and 21 creating a foil blank and a scrap matrix. The scrap matrix is peeled away from the carrier and wound on a foil waste rewind 22.

A conductive gel, which has been coated on a backing, is provided on a gel unwind roll 23. The preferred gel is Polyhesive®, manufactured by Valleylab in Boulder, Colo. The gel and backing are laminated together with the foil and carrier by rollers 24 and 25. The backing is stripped from the laminate by a stripping plate 26. A liner is unwound from a liner roll 27, and pressed onto the laminate by rollers 28 and 29.

The carrier is subsequently stripped away from the laminate by a stripping plate 30 and wound on a carrier waste rewind 31. A backing is unwound from a spool 32 and pressed against the laminate to form the layered sheet 16. The layered sheet 16 is fed through die cutting rollers 17 where the return pads 15 are cut out of the layered sheet 16. The scrap matrix is continuously fed to a scrap rewind 33.

Figure 3:
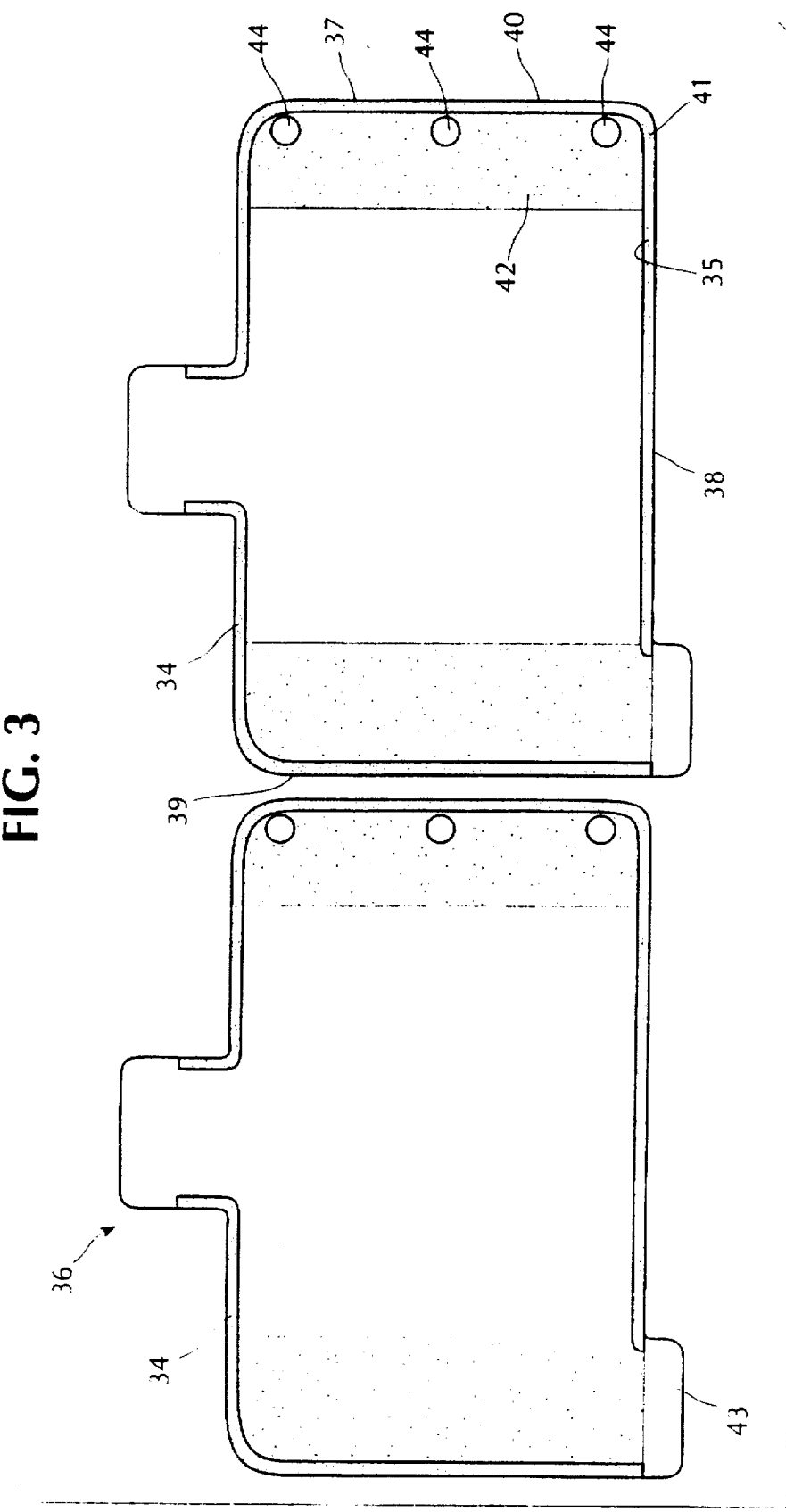
FIG. 3 is a perspective view of a die cutter, showing the location of the die packing material and the compressed air vents.

One of the inventive steps in the manufacturing process involves die cutting the layered sheet 16 with the die cutting rollers 17. A packing material 34 is placed on the inner edge 35 of the cutting die 36, as shown in FIG. 3. The purpose of the packing material 34 is to compress the gel 11 just prior to being cut. The compression causes the gel 11 to retract from the edge of the pad backing 13, thus creating a border area and insuring that no conductive gel 11 will reach the edge of the pad 15.

In the preferred embodiment, the die packing material 34 is an adhesive backed polyurethane manufactured by Boyd Corporation of Pleasanton, Calif. The thickness, width, and durometer of the die packing material must be adjusted to achieve the desired amount of retraction. The preferred embodiment has two layers of polyurethane. The bottom layer 41 is Boyd 4701-12-30, and is 0.125 inches thick. The bottom layer 41 is cut into gasket form and adhered around the entire inner edge of the die blade, with the leading edge 37, side edges 38, and all radius sections measuring 0.250 inches wide, and the trailing edge 39 section measuring 0.1875 inches wide. The top layer 42 is Boyd 4716-71, and is 0.062 inches thick. The top layer 42 is adhered over the top of the leading and trailing edge of the bottom layer 41, and is cut to 1.0 inch wide and fitted tightly against the blade 40. The top layer 42 and the bottom layer 41 have different durometers in the preferred embodiment.

The amount of retraction of the conductive gel 11 from the edge of the backing 13 is controlled in the preferred embodiment. Too much retraction was not desirable because it left portions of the conductive foil 12 exposed. Too little retraction was also not desirable because it increased the chance that gel 11 could reach the edge of the pad 15. In the preferred embodiment, the desired amount of retraction is in the range of 0.03 inches to 0.04 inches.

Skilled artisans will recognize that the particular geometry of the die packing material 34 is also dependent on the height of the cutting die 40. In the preferred embodiment, the cutting die is nominally 0.100 inches in height. Other arrangements of die packing material 34 are possible without departing from the spirit and scope of the present invention.

The top layer 42 of die packing material 34 is replaced after approximately one and a half hours of operation. The bottom layer 41 of die packing material is replaced after approximately three hours. This is because the packing material 34 eventually becomes compressed and loses its effectiveness. When replacing the die packing material 34, it is desirable to place it as close to the cutting die 40 as possible.

In the preferred embodiment, there is a pull tab 43 on the return pad to provide a convenient place to grab and remove the release liner from the conductive gel 11, as shown in FIG. 3. There is no die packing material 34 in the region of the pull tab since the pad backing 13 extends beyond the edge of the conductive gel 11, and therefore it is not necessary to retract gel 11 from the tab 43. The tab 43 is not shown in the embodiment of FIG. 2.

The thickness of the conductive gel layer 11 in the layered sheet 16 must also be controlled to achieve the desired retraction. In the preferred embodiment, the conductive gel 11 is controlled to a thickness between 0.036 and 0.042 inches. The nominal thickness of the gel roll stock, which includes the Polyhesive gel sandwiched between layers of commercial kraft paper, is 0.052 inches.

The preferred embodiment also has holes 44 for compressed air. The compressed air is forced against the pad blank and helps release it from the die 36.

The continuous rotary process described herein is applicable to the manufacture of an electrosurgical return pad 15. Many electrosurgical return pads are supplied with electrical cords attached. This disclosure does not apply to the process of attaching electrical cords.

While a particular preferred embodiment has been illustrated and described, the scope of protection sought is in the claims that follow.

What is claimed is:

1. A method of making a return pad for an electrosurgical system comprising the steps of: die cutting an electrically conductive foil on a backing using a rotary press to create a foil blank;

peeling the conductive foil from around the blank, and leaving the blank on its backing;

layering electrically conductive gel together with the die cut foil to form a layered sheet, and blanking the return pad from the layered sheet using a rotary die having cutting edges and a die packing material adjacent to at least a portion of the edges to compress the gel prior to cutting sufficient to cause the gel to retract after being cut.

2. The method according to claim 1 wherein the cutting edges have a pad side and a scrap matrix side, and there is an additional step of installing the die packing material on the pad side of the cutting edge.

3. The method according to claim 1 wherein the die has a leading edge and a trailing edge, and there is an additional step of installing packing material such that the material is wider on the leading edge of the die than on the trailing edge of the die.

4. The method according to claim 1 comprising the additional step of forcing compressed air around at least one edge of the cutting die to prevent the layered sheet from sticking to the die.

5. The method according to claim 1 wherein the packing material is comprised of two layers having different durometers.

6. The method according to claim 1 wherein the die packing material has sufficient thickness to cause retraction of the conductive gel, but does not cause retraction beyond the foil layer.

7. The method according to claim 1 wherein the die packing material is a foam with sufficient resilience in the form of closed cells to cause retraction of the conductive gel.

8. A method of making a return electrode for an electrosurgical system comprising the following steps:

die cutting conductive regions of foil adhered to a carrier;

peeling off from the carrier a scrap border of foil from the die cut foil about the conductive regions;

applying a layer of electrically conductive hydrogel over the foil and its carrier, the electrically conductive hydrogel carried on a support, the step of applying a layer forming a sandwich of the combination;

laminating the sandwich between a pair juxtaposed rollers to adhere them together as a laminate;

removing the support from the electrically conductive hydrogel of the laminate;

replacing the support with a liner over the electrically conductive hydrogel;

removing the carrier from beneath the foil;

replacing the carrier that has been removed with a film applied over the foil and to the electrically conductive hydrogel thereabove and about; and cutting the finished sandwich between a pair juxtaposed die cutting rollers while compressing portions of the electrically conductive hydrogel to stretch and reduce the thickness thereof during cutting to cause retraction of the hydrogel.

9. An apparatus for making a return pad for an electrosurgical system comprising:

a die cutting roller for die cutting an electrically conductive foil on a backing;

a take-up for peeling the scrap foil from its backing;

a rotary press for layering electrically conductive gel together with the die cut foil to form a layered sheet;

a second die cutting roller having edges for die cutting the layered sheet and, a die packing material around at least a portion of the cutting edges sufficient to compress the gel prior to cutting and cause the gel to retract after being cut.

10. The apparatus according to claim 9 wherein the edges on die cutting roller have an inner side and an outer side, and the packing material is disposed around the inner side of the cutting die.

11. The apparatus according to claim 9 wherein the die has a leading edge and a trailing edge, and the packing material is wider on the leading edge of the die than on the trailing edge of the die.

12. The apparatus according to claim 9 further comprising a compressed air port adjacent to at least one edge of the cutting die to prevent the layered sheet from sticking to the die.

13. The apparatus according to claim 9 wherein the packing material is comprised of two layers having different durometers.

14. The apparatus according to claim 9 wherein the die packing material has sufficient thickness to cause retraction of the conductive gel, but does not cause retraction beyond the foil layer.

15. The apparatus according to claim 9 wherein the die packing material is a foam with sufficient resilience in the form of closed cells to cause retraction of the conductive gel.

* * * * *